US012564679B2

(12) United States Patent
Lee et al.

(10) Patent No.: US 12,564,679 B2
(45) Date of Patent: Mar. 3, 2026

(54) ADJUSTING MEDICAMENT DELIVERY PARAMETERS IN AN OPEN LOOP MEDICAMENT DELIVERY MODE

(71) Applicant: Insulet Corporation, Acton, MA (US)

(72) Inventors: Joon Bok Lee, Acton, MA (US); Jason O'Connor, Acton, MA (US); Yibin Zheng, Hartland, WI (US); Jonathan Hardy, Reading, MA (US)

(73) Assignee: INSULET CORPORATION, Acton, MA (US)

( * ) Notice: Subject to any disclaimer, the term of this patent is extended or adjusted under 35 U.S.C. 154(b) by 538 days.

(21) Appl. No.: 18/119,062

(22) Filed: Mar. 8, 2023

(65) Prior Publication Data

US 2023/0285671 A1      Sep. 14, 2023

Related U.S. Application Data

(60) Provisional application No. 63/318,209, filed on Mar. 9, 2022.

(51) Int. Cl.
A61M 5/172      (2006.01)
G16H 20/17      (2018.01)

(52) U.S. Cl.
CPC .......... A61M 5/1723 (2013.01); G16H 20/17 (2018.01); *A61M 2230/201* (2013.01)

(58) Field of Classification Search
CPC .......... A61M 5/1723; A61M 2230/201; A61M 2005/14208; A61M 2205/33; G16H 20/17;

(Continued)

(56) References Cited

U.S. PATENT DOCUMENTS

| | | | |
|---|---|---|---|
| 303,013 | A | 8/1884 | Horton |
| 2,797,149 | A | 6/1957 | Skeggs |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Jason E Flick

(74) *Attorney, Agent, or Firm* — GOODWIN PROCTER LLP

(57) ABSTRACT

The exemplary embodiments provide an automated approach for adjusting the medicament delivery rate to the user when operating in an open loop manner ("open mode"). The approach relies upon an insulin delivery history to the user make adjustments to the medicament delivery rate in the open mode. In particular, the exemplary embodiments may look at the medicament delivery history while the medicament delivery device is operating in a closed loop manner ("closed mode") to determine how to adjust the open mode medicament delivery rate. It is presumed that in closed mode, the control system of the medicament device has gained knowledge over time about how to control the medicament delivery rate to produce good treatment outcomes for the user. The exemplary embodiments leverage this knowledge to adjust the open mode medicament delivery rates. Medicament bolus deliveries in open mode may also be adjusted in like fashion.

20 Claims, 10 Drawing Sheets

600

Basal Open Loop Adjust

602 — Determine Average Amount of Basal Medicament Deliveries Over Period of Days During Segment of Time in Closed Loop Mode 604 — Determine Average Amount of Basal Medicament Programmed to be Delivered During Segment of Time in Open Loop Mode 606 — Compare Open Loop Average for Segment with Closed Loop Average for the Segment 608 — Based of the Comparison, Determine Change in Amount of Basal Medicament Programmed to be Delivered During Segment of Time in Open Loop Mode 610 — Display a Suggestion of the Determined Change in Amount of Basal Medicament Programmed to be Delivered During Segment of Time in Open Loop Mode 612 — Programmatically Make the Determined Change in Amount of Basal Medicament Programmed to be Delivered During Segment of Time in Open Loop Mode Done

(58) Field of Classification Search
CPC .... G16H 20/10; A61B 5/4839; A61B 5/7275;
A61B 5/4848; A61B 5/7271; A61B
5/4836; A61B 5/486; A61B 5/4833
See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |

(56) References Cited

U.S. PATENT DOCUMENTS

| | | | |
|---|---|---|---|
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B2 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |

(56)  References Cited

U.S. PATENT DOCUMENTS

| | | |
|---|---|---|
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |

(56) References Cited

U.S. PATENT DOCUMENTS

| | | |
|---|---|---|
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1* | 6/2014 | Finan ................... G16H 20/17 |
| | | 604/504 |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |

| | | |
|---|---|---|
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0317743 A1* | 11/2016 | Estes ..................... G16H 20/17 |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1* | 7/2018 | Desborough ...... A61B 5/14532 |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |

(56)                   References Cited

FOREIGN PATENT DOCUMENTS

| | | | |
|---|---|---|---|
| JP | 51125993 | A | 11/1976 |
| JP | 02131777 | A | 5/1990 |
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 200032258 | A1 | 6/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2016176251 | A1 | 11/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

(56) References Cited

OTHER PUBLICATIONS

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor, Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

(56)             References Cited

OTHER PUBLICATIONS

International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type 1 diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.

* cited by examiner

300

Create Basal Profile

302

User Specifies Segment Lengths and Basal Rate for Segments

304

Values are Saved in Basal Profile

306

Use Basal Profile in Open Loop Mode

Done

600

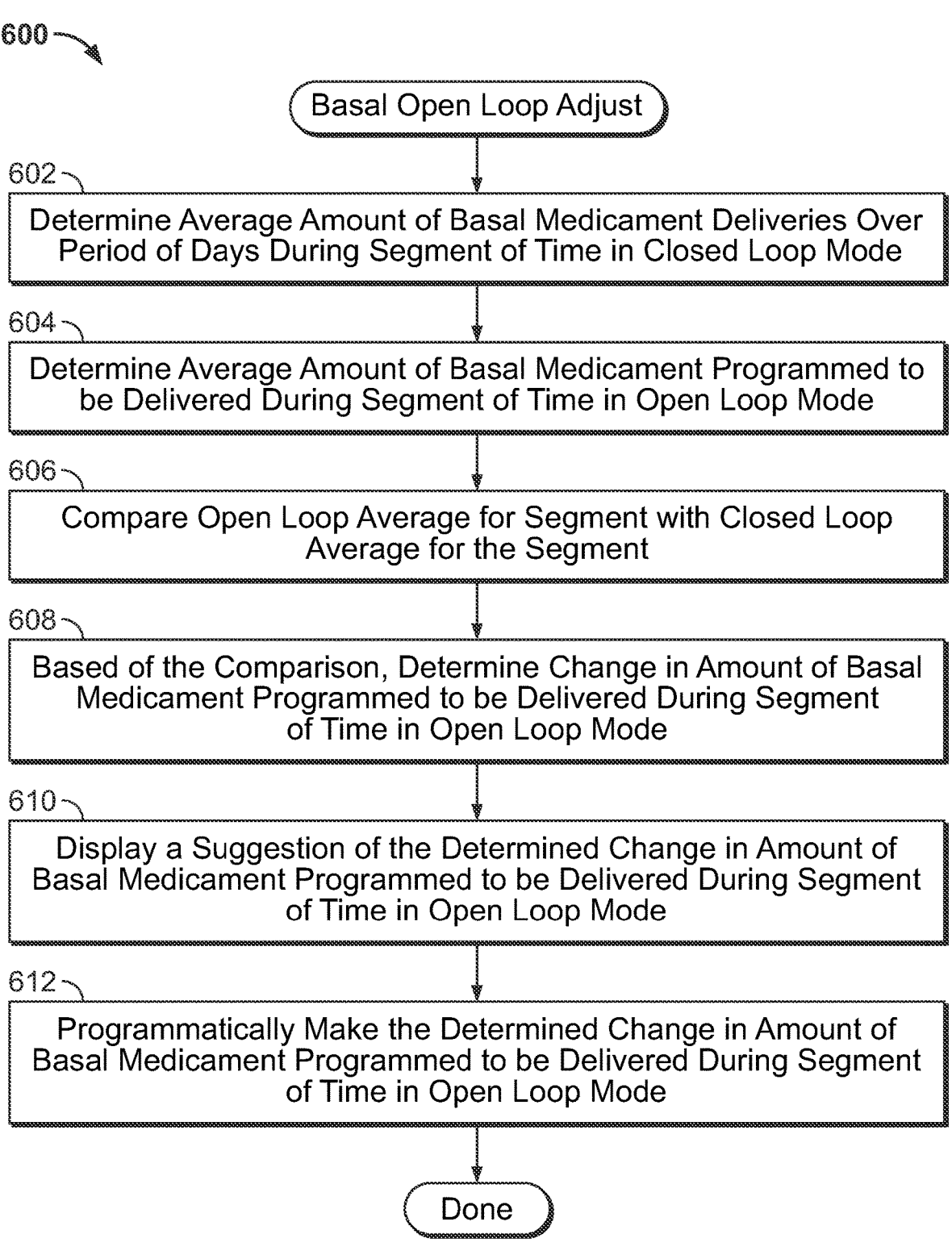

Basal Open Loop Adjust

602

Determine Average Amount of Basal Medicament Deliveries Over Period of Days During Segment of Time in Closed Loop Mode

604

Determine Average Amount of Basal Medicament Programmed to be Delivered During Segment of Time in Open Loop Mode

606

Compare Open Loop Average for Segment with Closed Loop Average for the Segment

608

Based of the Comparison, Determine Change in Amount of Basal Medicament Programmed to be Delivered During Segment of Time in Open Loop Mode

610

Display a Suggestion of the Determined Change in Amount of Basal Medicament Programmed to be Delivered During Segment of Time in Open Loop Mode

612

Programmatically Make the Determined Change in Amount of Basal Medicament Programmed to be Delivered During Segment of Time in Open Loop Mode Done

Change in Basal
Profile

Current Basal Rate: 0.75 u/hr — 622

Rec Basal Rate: 1.00 u/hr — 624

Delta of Rate: + 0.25 u/hr — 626

628

Accept

630

Cancel

700

Determine Recommendation Option 1

702 —

Calculate the Average of the Open Loop Average and the Closed Loop Average and Assign as Recommended Dosage for Delivery During the Segment

704 —

Assign Weights to Recommended Dosage and Open Loop Average

706 —

Sum the Weighted Recommended Dosage and Weighted Open Loop Average

708 —

Adjust to Make an Hourly Rate

Done

800

Determine Recommendation Option 2

802
Determine a Range of the Difference of the Closed Loop Average Relative to the Open Loop Average 804
Based on the Determined Range, Assign a Delta Value 806
Determine a Recommended Adjustment Amount from the Delta Value 808
Sum the Weighted Recommended Dosage and Weighted Open Loop Average 810
Adjust to Make an Hourly Rate Done

900

ADJUSTING MEDICAMENT DELIVERY PARAMETERS IN AN OPEN LOOP MEDICAMENT DELIVERY MODE

RELATED APPLICATIONS

This application claims the benefit of U.S. Provisional Patent Application No. 63/318,209, filed Mar. 9, 2022, the contents of which are incorporated herein by reference in their entirety.

BACKGROUND

Conventional medicament delivery devices may operate in a closed loop manner and/or an open loop manner. In the closed loop manner, a feedback loop is provided to adjust a delivery rate to achieve a target objective. For example, where the medicament delivery device is an insulin delivery device, the objective may be to obtain a target glucose level for a user. The difference between a current glucose level and the target glucose level may be fed back to adjust the medicament delivery rate. When a medicament delivery device operates in the open loop manner, the user provides inputs to the medicament delivery device that determine the dosage of delivery of the medicament delivery. For example, the user may specify the medicament delivery amounts explicitly in inputs. The inputs may be used to create a profile that is stored and used by the medicament delivery device when operating in the open loop manner.

One of the drawbacks for operating a medicament delivery device in an open loop manner is that users tend to select medicament delivery dosages that are sub-optimal. For instance, with insulin delivery devices operating in an open loop manner, users tend to underestimate their insulin needs and choose too low of medicament delivery dosage. As a result, users have less than optimal glucose control, and users tend to deliver insulin boluses more as a result. The increased delivery of insulin boluses increases the risk of the user suffering from hypoglycemia.

SUMMARY

In accordance with a first inventive aspect, a non-transitory storage medium stores instructions executable by a processor of an electronic device having a display to cause the processor to, for a medicament delivery device that operates in an open loop mode and a closed loop mode, determine a first average, which is an average over a period of a total basal delivery amount of medicament that is delivered to a user by the medicament delivery device in the closed loop mode during a same segment of time in each interval the period. The interval may be a day, multiple days, hours, etc. The instructions also cause the processor to compare the first average with an amount of medicament that is programmed to be delivered by the medicament delivery device to the user for the segment of time in the open loop mode to determine a difference. The instructions additionally cause the processor to, based on the comparing, perform the following: display on the display a suggestion of a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference.

The medicament may be one of insulin, glucagon like peptide-1 (GLP-1), pramlintide, a co-formulation of any of the foregoing, or another agent affecting glucose level. The programmatically causing the amount of medicament that is programmed to be delivered to the user by the medicament delivery device for the segment of time in the open loop mode to be adjusted may include calculating a second average of the first average with the amount of the medicament that is programmed to be delivered by the medicament delivery device to the user for the segment of time in the open loop mode, and adjusting the amount of the medicament that is programmed to be delivered to the user by the medicament delivery device for the segment of time in the open loop mode based on the second average to produce an adjusted amount of the medicament that is programmed to be delivered to the user by the medicament delivery device for the segment of time in the open loop mode. The adjusting of the amount that is programmed to be delivered to the user by the medicament delivery device for the segment of time in the open loop mode based on the second average to produce an adjusted amount may include adding a weighted version of the amount of the medicament that is programmed to be delivered to the user by the medicament delivery device for the segment of time in the open loop mode with a weighted version of the second average to produce an adjusted amount of the medicament that is programmed to be delivered to the user by the medicament delivery device for the segment of time in the open loop mode to produce the adjusted amount of the medicament.

A magnitude of the adjusting of the amount of the medicament that is programmed to be delivered to the user by the medicament delivery device for the segment of time in the open loop mode to reduce the difference may depend on a magnitude of the difference or a magnitude of the suggested adjusting in the suggestion of the amount of the medicament that is programmed to be delivered to the user by the medicament delivery device for the segment of time in the open loop mode to reduce the difference may depend on the magnitude of the difference. The non-transitory storage medium may further store instructions that cause the processor to: define a plurality of ranges of possible values for the difference, define a change amount for each range, determine a selected one of the ranges that the difference falls into, and wherein either the suggestion of the change in the amount of the medicament suggests the change amount of the selected one of the ranges or the programmatically causing the amount of the medicament that is programmed to be delivered to the user by the medicament delivery device for the segment of time in the open loop mode is adjusted by the change amount of the selected one of the ranges. If the programmatically causing the amount of the medicament that is programmed to be delivered to the user by the medicament delivery device for the segment of time in the open loop mode to be adjusted to reduce the difference is performed, the non-transitory storage medium further may store instructions that cause the processor to display a magnitude of the adjusting of the amount of the medicament that is programmed to be delivered to the user by the medicament delivery device for the segment of time in the open loop mode on the display.

In accordance with another inventive aspect, an electronic device is provided that includes a non-transitory storage media for storing computer programming instructions and a processor. The processor is configured to execute the computer programming instructions to cause the processor to, for a medicament delivery device that operates in an open loop mode and a closed loop mode, determine a first average which is an average over a period of a total basal delivery amount of medicament that is delivered to a user by the medicament delivery device in the closed loop mode during a same segment of time in intervals in the period. The instructions also cause the processor to compare the first average with an amount of medicament that is programmed to be delivered by the medicament delivery device to the user for the segment of time in the open loop mode to determine a difference. The instructions further cause the processor to, based on the comparing, perform the following: display on the display a suggestion of a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference.

The electronic device may be one of the medicament delivery device or a management device for the medicament delivery device. The medicament may be one of insulin, glucagon like peptide-1 (GLP-1), pramlintide or another agent affecting glucose level. The processor configured to programmatically causing the amount of medicament that is programmed to be delivered to the user by the medicament delivery device for the segment of time in the open loop mode to be adjusted may comprise the processor being configured to: calculate a second average which is an average of the first average with the amount of the medicament that is programmed to be delivered by the medicament delivery device to the user for the segment of time in the open loop mode, and adjust the amount of the medicament that is programmed to be delivered to the user by the medicament delivery device for the segment of time in the open loop mode based on the second average to produce an adjusted amount of the medicament that is programmed to be delivered to the user by the medicament delivery device for the segment of time in the open loop mode. A magnitude of the adjusting of the amount of the medicament that is programmed to be delivered to the user by the medicament delivery device for the segment of time in the open loop mode to reduce the difference may depend on a magnitude of the difference or a magnitude of the suggested adjusting in the suggestion of the amount of the medicament that is programmed to be delivered to the user by the medicament delivery device for the segment of time in the open loop mode to reduce the difference may depend on the magnitude of the difference.

The processor may be further configured to execute additional programming instructions to: define a plurality of ranges of possible values for the difference, define a change amount for each range and determine a selected one of the ranges that the difference falls into; and either the suggestion of the change in the amount of the medicament may suggest the change amount of the selected one of the ranges or the programmatically causing the amount of the medicament that is programmed to be delivered to the user by the medicament delivery device for the segment of time in the open loop mode may be adjusted by the change amount of the selected one of the ranges. If the programmatically causing the amount of the medicament that is programmed to be delivered to the user by the medicament delivery device for the segment of time in the open loop mode to be adjusted to reduce the difference is performed, the processor may further be configured to execute programming instructions to display a magnitude of the adjusting of the amount of the medicament that is programmed to be delivered to the user by the medicament delivery device for the segment of time in the open loop mode on the display.

In accordance with an additional inventive aspect non-transitory storage medium storing instructions executable by a processor of an electronic device having a display to cause the processor to, for a medicament delivery device that operates in an open loop mode and a closed loop mode, determine an average over a period of a total basal delivery amount of medicament that is delivered to a user by the medicament delivery device in the closed loop mode during a same segment of time in intervals in the period and compare the average with an amount of medicament that is programmed to be delivered by the medicament delivery device to the user for the segment of time in the open loop mode to determine a difference. The instructions further cause the processor to, based on the determined difference, adjust at least one of the insulin to carbohydrate ratio (ICR) of the user or the correction factor of the user and use the adjusted ICR of the user or the adjusted correction factor of the user in determining a recommended bolus dosage of medicament for the user.

Both the ICR of the user and the correction factor of the user may be adjusted in the adjusting. The non-transitory storage medium may store programming instructions to cause the processor to, based on the comparing, perform the following: display on the display a suggestion of a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference. The programming instructions may cause the processor to perform both the displaying on the display of the suggestion and the programmatically causing the amount of medicament that is programmed to be delivered to the user by the medicament delivery device for the segment of time in the open loop mode to be adjusted to reduce the difference. The medicament may be one of insulin, glucagon like peptide-1 (GLP-1), pramlintide or another agent affecting glucose level. The processor may be part of a management device for the medicament delivery device.

BRIEF DESCRIPTION OF THE DRAWINGS

FIG. 6A depicts a flowchart of illustrative steps that may be performed in exemplary embodiments to adjust delivery rates for open loop basal delivery.

DETAILED DESCRIPTION

The exemplary embodiments provide an automated approach for adjusting the medicament delivery amounts to the user when operating in a manual or an open loop manner ("open loop mode"). The approach relies upon an insulin delivery history to the user make adjustments to the medicament delivery amounts in the open loop mode. In particular, the exemplary embodiments may look at the medicament delivery history while the medicament delivery device is operating in a closed loop manner ("closed loop mode") to determine how to adjust the open loop mode medicament delivery amounts. In closed loop mode, the control system of the medicament device gains knowledge over time about how to control the medicament delivery rate to produce more optimal treatment outcomes for the user. The exemplary embodiments leverage this knowledge to adjust the open loop mode medicament delivery amounts. These amounts may be expressed as hourly delivery rates in some embodiments, but other units may be used.

The adjustments may help the performance of the treatment provided by the medicament delivery device. For example, for an insulin delivery device, the adjustments may result in better glucose control for the user while the insulin delivery device is operating in open loop mode. The adjustments may also reduce the number of boluses needed by the user and hence, reduce the risk of hypoglycemia to the user.

In some exemplary embodiments, the medicament delivery amounts that are adjusted are those for basal medicament deliveries in open loop mode (e.g., according to a user's basal profile) that occur at regular intervals each cycle (where a cycle may be, for instance, a 5-minute interval) on an ongoing basis, though the rate may be in units of medicament units per hour. However, the exemplary embodiments may also alter medicament bolus dosages as well in a proportional manner. For the case where the medicament is insulin, the control system may adjust the insulin to carbohydrate ratio (ICR) for the user and the correction factor (CF) for the user in an amount that is proportional to the adjustment amount to the basal medicament delivery rate in open loop mode. Thus, if the basal medicament delivery rate is adjusted up by 10%, the ICR and CF for the user are adjusted up by 10%.

Figure 1:
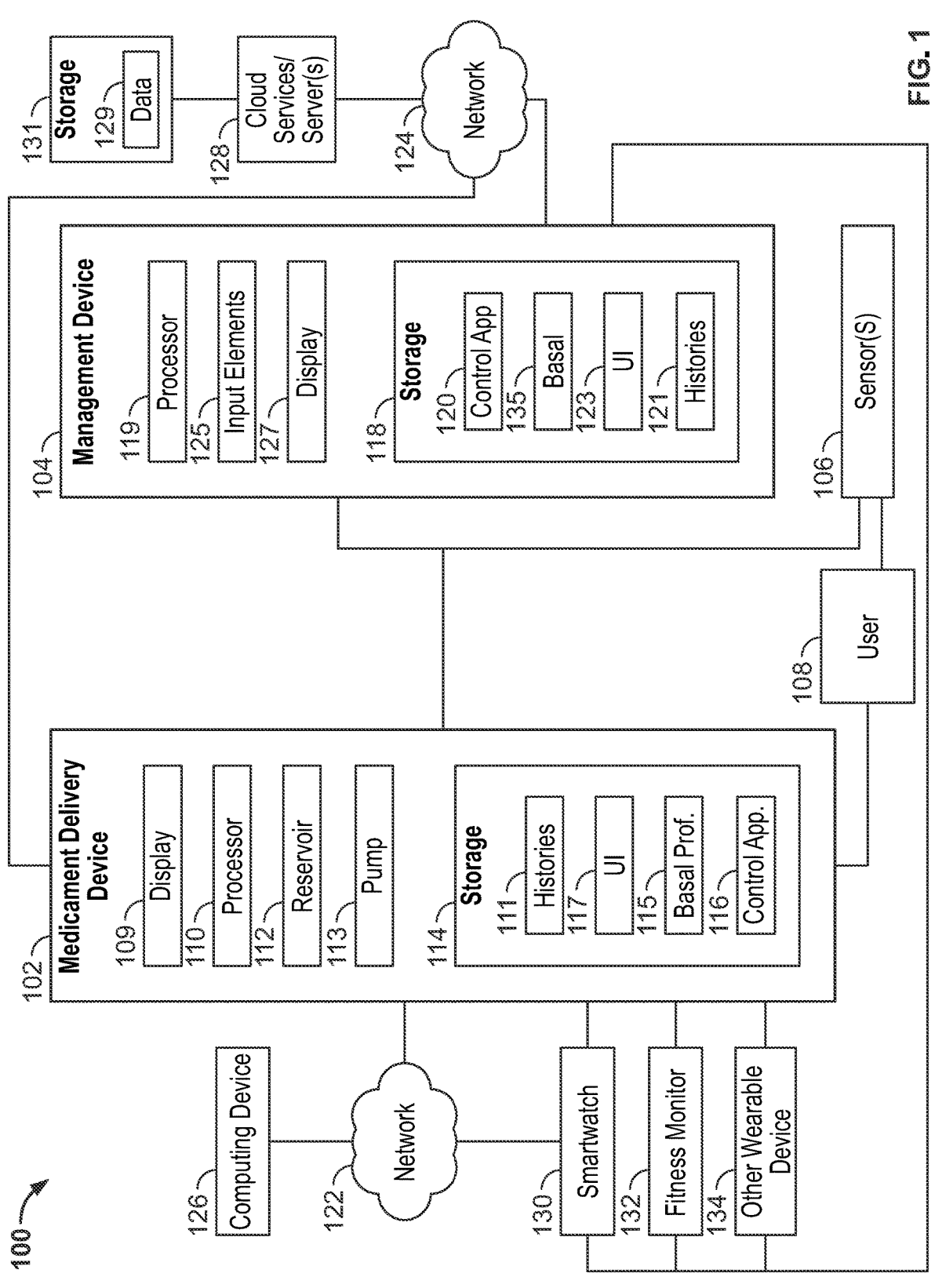
FIG. 1 depicts an illustrative medicament delivery system suitable for exemplary embodiments.

FIG. 1 depicts an illustrative medicament delivery system 100 that is suitable for delivering a medicament to a user 108 in accordance with the exemplary embodiments. The medicament delivery system 100 includes a medicament delivery device 102. The medicament delivery device 102 may be a wearable device that is worn on the body of the user 108 or carried by the user. The medicament delivery device 102 may be directly coupled to a user (e.g., directly attached to a body part and/or skin of the user 108 via an adhesive or the like) or carried by the user (e.g., on a belt or in a pocket) with the medicament delivery device 102 being connected to an infusion site where the medicament is injected using a needle and/or cannula. In a preferred embodiment, a surface of the medicament delivery device 102 may include an adhesive to facilitate attachment to the user 108.

The medicament delivery device 102 may include a processor 110. The processor 110 may be, for example, a microprocessor, a logic circuit, a field programmable gate array (FPGA), an application specific integrated circuit (ASIC) or a microcontroller. The processor 110 may maintain a date and time as well as other functions (e.g., calculations or the like). The processor 110 may be operable to execute a control application 116 encoded in computer programming instructions stored in the storage 114 that enables the processor 110 to direct operation of the medicament delivery device 102. The control application 116 may be a single program, multiple programs, modules, libraries or the like. The processor 110 also may execute computer programming instructions stored in the storage 114 for a user interface 117 that may include one or more display screens shown on display 109. The display 109 may display information to the user 108 and, in some instances, may receive input from the user 108, such as when the display 109 is a touchscreen.

The control application 116 may control delivery of a medicament to the user 108 per a control approach like that described herein. The storage 114 may hold histories 111 for a user, such as a history of basal deliveries, a history of bolus deliveries, and/or other histories, such as a meal event history, exercise event history, glucose level history and/or the like. The storage 114 also may include one or more basal profiles 115 that are used when the medicament delivery device is operating in open loop mode. In addition, the processor 110 may be operable to receive data or information. The storage 114 may include both primary memory and secondary memory. The storage 114 may include random access memory (RAM), read only memory (ROM), optical storage, magnetic storage, removable storage media, solid state storage or the like.

The medicament delivery device 102 may include one or more housings for housing its various components including a pump 113, a power source (not shown), and a reservoir 112 for storing a medicament for delivery to the user 108. A fluid path to the user 108 may be provided, and the medicament delivery device 102 may expel the medicament from the reservoir 112 to deliver the medicament to the user 108 using the pump 113 via the fluid path. The fluid path may, for example, include tubing coupling the medicament delivery device 102 to the user 108 (e.g., tubing coupling a cannula to the reservoir 112), and may include a conduit to a separate infusion site.

There may be one or more communications links with one or more devices physically separated from the medicament delivery device 102 including, for example, a management device 104 of the user and/or a caregiver of the user, a sensor 106, a smartwatch 130, a fitness monitor 132 and/or another variety of wearable device 134. The communication links may include any wired or wireless communication links operating according to any known communications protocol or standard, such as Bluetooth®, Wi-Fi, a near-field communication standard, a cellular standard, or any other wireless protocol.

The medicament delivery device 102 may interface with a network 122 via a wired or wireless communications link. The network 122 may include a local area network (LAN), a wide area network (WAN) or a combination therein. A computing device 126 may be interfaced with the network, and the computing device may communicate with the medicament delivery device 102.

The medicament delivery system 100 may include one or more sensor(s) 106 for sensing the levels of one or more analytes. The sensor(s) 106 may be coupled to the user 108 by, for example, adhesive or the like and may provide information or data on one or more medical conditions and/or physical attributes of the user 108. The sensor(s) 106 may be physically separate from the medicament delivery device 102 or may be an integrated component thereof.

The medicament delivery system 100 may or may not also include a management device 104. In some embodiments, no management device is not needed as the medicament delivery device 102 may manage itself. The management device 104 may be a special purpose device, such as a dedicated personal diabetes manager (PDM) device. The management device 104 may be a programmed general-purpose device, such as any portable electronic device including, for example, a dedicated controller, such as a processor, a micro-controller, or the like. The management device 104 may be used to program or adjust operation of the medicament delivery device 102 and/or the sensors 106. The management device 104 may be any portable electronic device including, for example, a dedicated device, a smartphone, a smartwatch or a tablet. In the depicted example, the management device 104 may include a processor 119 and a storage 118. The processor 119 may execute processes to manage a user's glucose levels and to control the delivery of the medicament to the user 108. The medicament delivery device 102 may provide data from the sensors 106 and other data to the management device 104. The data may be stored in the storage 118. The processor 119 may also be operable to execute programming code stored in the storage 118. For example, the storage 118 may be operable to store one or more control applications 120 for execution by the processor 119. The one or more control applications 120 may be responsible for controlling the medicament delivery device 102, such as by controlling the AID delivery of insulin to the user 108. The storage 118 may store the one or more control applications 120, histories 121 like those described above for the medicament delivery device 102, one or more basal profiles 135 and other data and/or programs.

A display 127, such as a touchscreen, may be provided for displaying information. The display 127 may display user interface (UI) 123. The display 127 also may be used to receive input, such as when it is a touchscreen. The management device 104 may further include input elements 125, such as a keyboard, button, knobs, or the like, for receiving input form the user 108.

The management device 104 may interface with a network 124, such as a LAN or WAN or combination of such networks via wired or wireless communication links. The management device 104 may communicate over network 124 with one or more servers or cloud services 128. Data, such as sensor values, may be sent, in some embodiments, for storage and processing from the medicament delivery device 102 directly to the cloud services/server(s) 128 or instead from the management device 104 to the cloud services/server(s) 128. The cloud services/server(s) 128 may provide output from the model 115 as needed to the management device 104 and/or medicament delivery device 102 during operation.

Other devices, like smartwatch 130, fitness monitor 132 and wearable device 134 may be part of the medicament delivery system 100. These devices 130, 132 and 134 may communicate with the medicament delivery device 102 and/or management device 104 to receive information and/or issue commands to the medicament delivery device 102. These devices 130, 132 and 134 may execute computer programming instructions to perform some of the control functions otherwise performed by processor 110 or processor 119, such as via control applications 116 and 120. These devices 130, 132 and 134 may include displays for displaying information. The displays may show a user interface for providing input by the user, such as to request a change or pause in dosage or to request, initiate, or confirm delivery of a bolus of a medicament, or for displaying output, such as a change in dosage (e.g., of a basal delivery amount) as determined by processor 110 or management device 104. These devices 130, 132 and 134 may also have wireless communication connections with the sensor 106 to directly receive analyte measurement data.

A wide variety of medicaments may be delivered by the medicament delivery device 102. The medicament may be insulin for treating diabetes. The medicament may be glucagon for raising a user's glucose level. The medicament may also be a glucagon-like peptide (GLP)-1 receptor agonists for lowering glucose or slowing gastric emptying, thereby delaying spikes in glucose after a meal. Alternatively, the medicament delivered by the medicament delivery device 102 may be one of a pain relief agent, a chemotherapy agent, an antibiotic, a blood thinning agent, a hormone, a blood pressure lowering agent, an antidepressant, an antipsychotic, a statin, an anticoagulant, an anticonvulsant, an antihistamine, an anti-inflammatory, a steroid, an immunosuppressive agent, an antianxiety agent, an antiviral agents, a nutritional supplement or a vitamin.

The functionality described below for the exemplary embodiments may be under the control of or performed by the control application 116 of the medicament delivery device 102 or the control application 120 of the management device 104. In some embodiments, the functionality may be under the control of or performed by the cloud services or servers 128, the computing device 126 or by the other enumerated devices, including smartwatch 130, fitness monitor 132 or another wearable device 134.

The medicament delivery device 102 may operate in an open loop mode and in a closed loop mode. In the open loop mode, the user 108 manually inputs the amount of medicament to be delivered (such as per hour) for segments of the day. The inputs may be stored in a basal profile 115, 135 for the user 108. In other embodiments, a basal profile may not be used. The control application 116, 120 uses the input information from the basal profile 115, 135 to control basal medicament deliveries in open loop mode. In contrast, in the closed loop mode, the control application 116, 120 determines the medicant delivery amount for the user 108 on an ongoing basis based on a feedback loop. For an insulin delivery device, the aim of the closed loop mode is to have the user's glucose level at a target glucose level.

Figure 2:
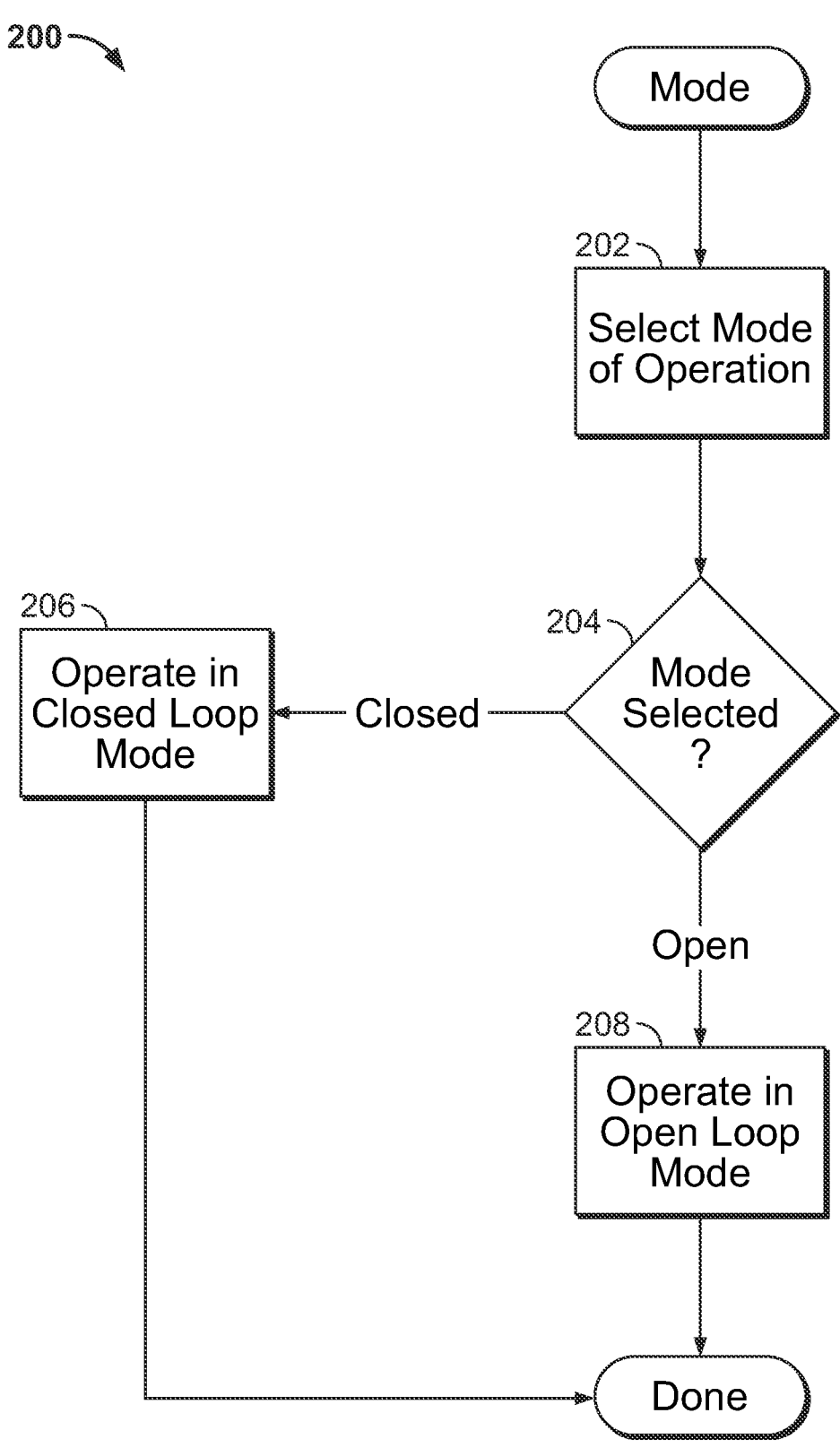
FIG. 2 depicts a flowchart of illustrative steps that may be performed by exemplary embodiments in selecting whether to operate in an open loop mode or a closed loop mode.

FIG. 2 depicts a flowchart 200 of illustrative steps that may be used in selecting a mode in some exemplary embodiments. At 202, user and/or the control application 116, 120 may select the mode. For instance, the user interface 117, 123 may include a user interface element, like a button or menu item, that allows the user 108 to change the current mode. The medicament delivery device 102 may have a default mode, such as the closed loop mode. At 204, based upon the selection, the control application 116, 120 determines the proper mode. At 206, if the closed loop mode is selected, the medicament delivery device operates in the closed loop mode. At 208, if the open loop mode is selected, the medicament delivery device 102 operates in the closed loop mode.

Figure 3:
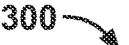
FIG. 3 depicts a flowchart of illustrative steps that may be performed in exemplary embodiments to create a basal profile.
Figure 3:
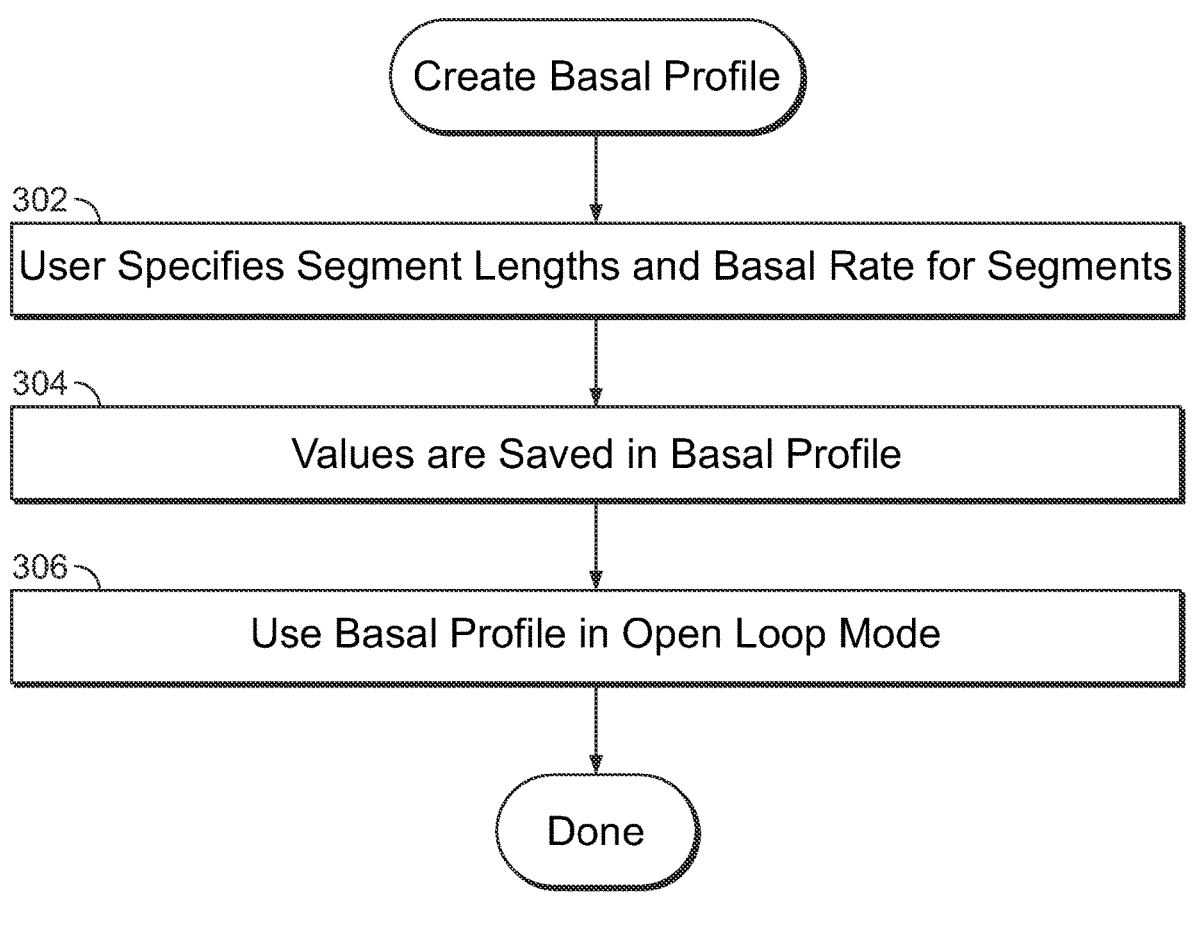
Figures 4A, 4B:
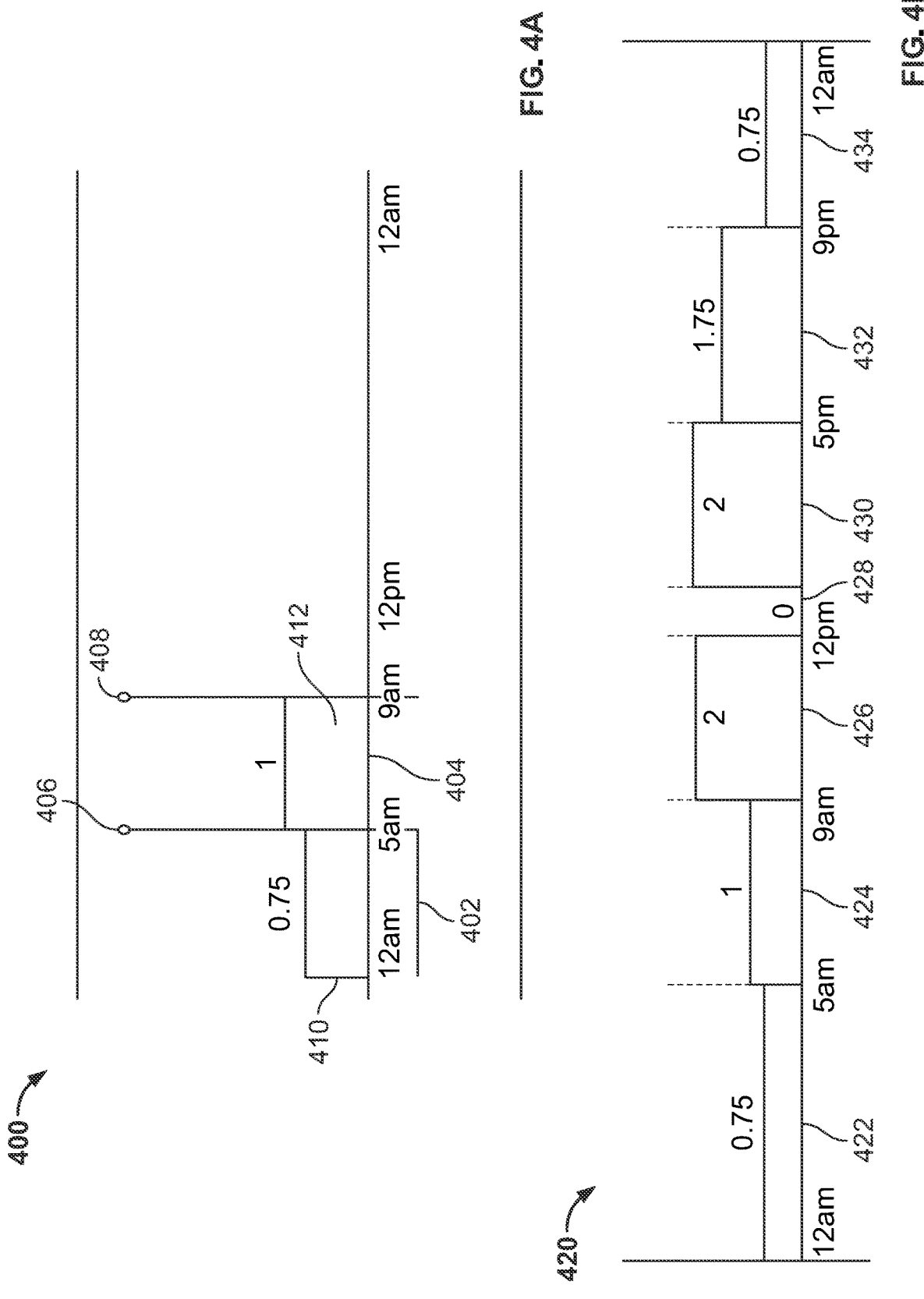
FIG. 4A depicts an illustrative user interface of an exemplary embodiment that may be used in generating a basal profile.
FIG. 4B depicts a graphical depiction of an illustrative basal profile.

As mentioned above, in some exemplary embodiments, open loop mode uses a basal profile 115, 135 to guide medicament deliveries in open loop mode. FIG. 3 depicts a flowchart 300 of illustrative steps that may be performed to create a basal profile 115, 135 for the user 108. It should be appreciated that the user 108 may have multiple basal profiles 115, 135 and may select among them when operating in open loop mode. The user interface 117, 123 may provide options for the user to create a basal profile 115, 135. At 302, the user specifies segment lengths and basal medicament delivery rates for the segments. Each segment is a period of time, whose length is specified by the user 108. FIG. 4A depicts an example user interface 400 where a user 108 has begun to create a basal profile. In the depicted example, the user 108 has defined medicament delivery rates for segment 402 and segment 404. The first segment 402 begins at 12 am and continues to 5 am, where the second segment 404 runs from 5 am to 9 am. The user 108 may specify the length of each segment, such as by dragging bars 406 and 408 along a timeline to specify the start time and end time for the segment. The user 108 also enters the delivery rate over the specified segment time frame and the user may do this by entering numerical numbers on a numerical user interface or by adjusting the height of a bar (for example) on the user interface by dragging a top of the bar up or down with the user's finger. By way of example, the medicament delivery rate for segment 402 is 0.75 units per hour as indicated by the height of the graphic bar 410, whereas the medicament delivery rate for segment 404 is 1.0 unit per hour as indicated by the height of graphic bar 412. This process is repeated for remaining segments of a day to cover all 24 hours of the day. FIG. 4B shows an illustrative completed profile 420 having segments 422, 424, 426, 428, 430, 432 and 434.

At 304, the values for the segment length and the associated hourly medicament delivery rates for the segments that have been specified by the user are stored in a basal profile 115, 135. At 306, the basal profile is used by the control application 116, 120 in open loop mode. Thus, suppose that the basal profile 420 of FIG. 4B is used for a user in manual mode or open loop mode. In that case, the control application 116, 120 sets the basal medicament delivery rate at 0.75 units between 12 am and 5 am. At 5 am, the control application 116, 120 boosts the delivery rate to 1.0 unit per hour until 9 am.

Figure 5:
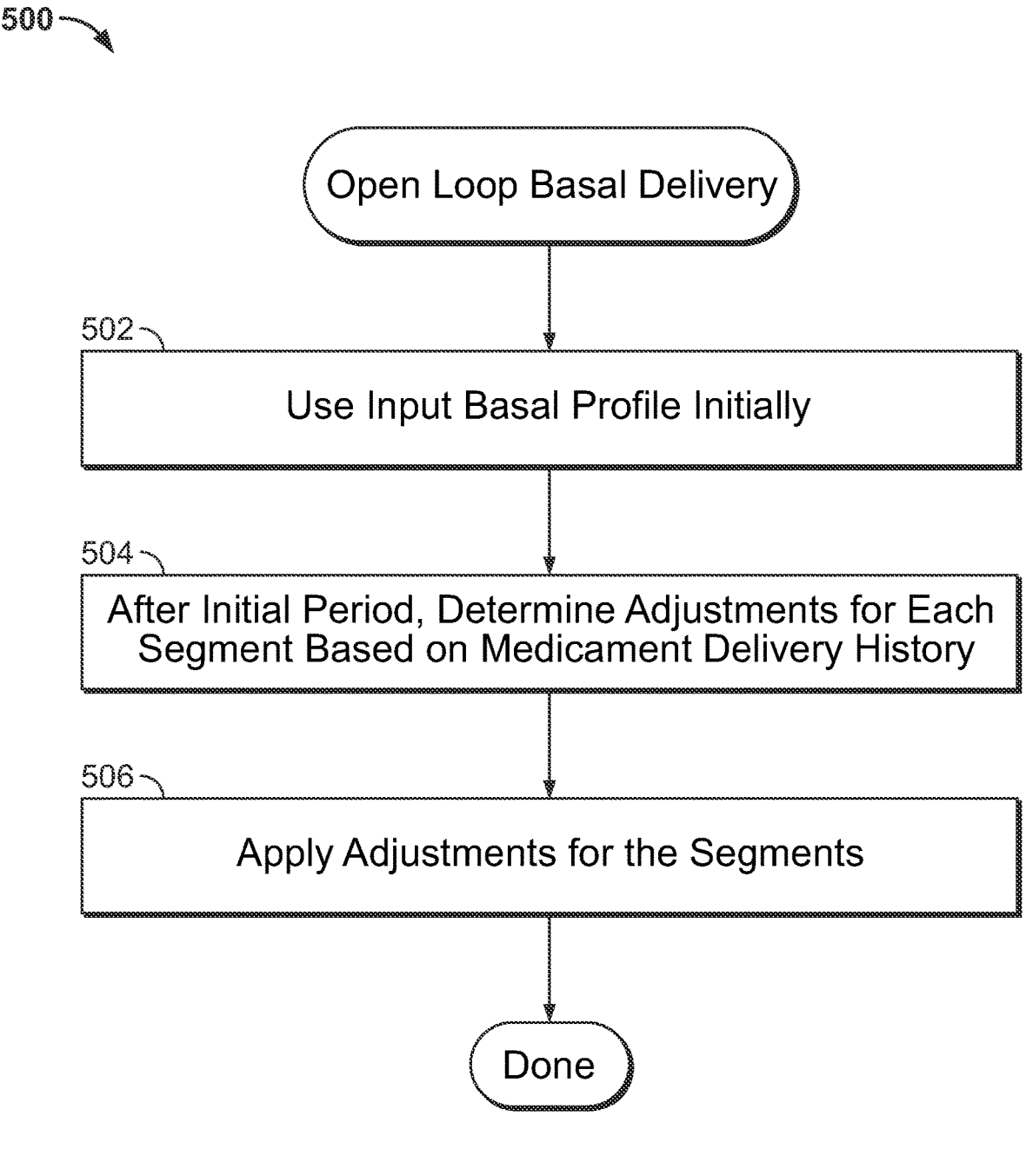
FIG. 5 depicts a flowchart of illustrative steps that may be performed in exemplary embodiments to perform open loop basal delivery.

As mentioned above, the exemplary embodiments may adjust the user-input hourly medicament delivery rates. In some embodiments, the adjusted values may be stored in a corrected basal profile stored with the basal profiles 115, 135, and corrected basal profile may be used by the control application 116, 120 when operating in open loop mode. FIG. 5 depicts a flowchart 500 of illustrative steps that may be performed in exemplary embodiments to make adjustments to the medicament delivery amounts provided by the user 108. At 502, the user enters the values for incorporation in the basal profile 115, 135 to set the medicament delivery amounts of the medicament delivery device. Subsequently, at 504, adjustments to the medicament delivery amounts used in open loop mode may be made based on the medicament delivery history in closed loop mode. For example, after 48 hours of operation in closed loop mode, there is sufficient medicament delivery history to rely upon for making adjustments. Hence, adjustments can be made after that time of operation. At 506, the adjustments are made for the medicament delivery amounts (e.g., delivery amounts per hour) specified by the basal profile 115, 135. These adjustments may be made to the basal profile 115, 135 or to the actual value that is set by the control application 116, 120 for the medicament delivery amounts. The adjustment may be triggered by a transition from closed loop mode to open loop mode, may be triggered at regular intervals, such as every day, every 12 hours, or another period, or may be triggered by specific events, such as hypoglycemic and/or hyperglycemic events that may occur throughout the day or week.

FIG. 6A depicts a flowchart 600 of illustrative steps that may be performed in exemplary embodiments to determine and to make adjustments to the medicament delivery amounts specified in the basal profile 115, 135. The aim of making the adjustments is to improve the performance of the medicament delivery device 102 in open loop mode by choosing medicament delivery rates that are better suited to the user 108. The exemplary embodiments rely upon medicament delivery rate history in the closed loop mode to determine what an appropriate medicament delivery amount is and to calculate the magnitude of adjustments that need to be made. At 602, the average amount of basal medicament deliveries over a period of intervals, such as days, during a segment of time in closed loop mode is calculated. For an insulin delivery device, this average $TOT_{AID}(j)$ may be calculated as:

$$TOT_{AID}(j) = \frac{\sum_{k=1}^{m} M_{AID}(j)}{m}$$

where $$M_{AID}(j) = \sum_{i=t_{start,j}}^{t_{end,j}} I_k(i)$$

and where m is the number of days in the period over which $I_k(i)$ is summed, and $I_k(i)$ is the amount of basal insulin delivered to the user 108 during cycle i in segment j, whether by manual delivery or by automated insulin delivery from an algorithm.

At 604, the amount of basal medicament to be delivered during the segment of time to be delivered during the segment of time in open loop mode is determined. For the segment j, the total amount of medicament delivered during the segment is determined. This step entails looking up the delivery rate for the medicament in open loop mode in the basal profile. Where the medicament is insulin, the amount of basal metabolic medicament in open loop may be expressed as:

$$TOT_{manual}(j) = h_j \cdot M_{man}(j)$$

where $h_j$ is the number of hours in the segment j and $M_{man}(j)$ is the hourly insulin delivery rate for the segment j.

At 606, the determined open loop amount is compared with the closed loop average for the segment. At 608, based on the comparison of the determined open loop amount with the closed loop average, a change amount for the basal medicament delivery rate during the segment in open loop mode is determined, as will be detailed below. In general, the magnitude of the change amount is reflective of the magnitude of the difference between the open loop amount and the closed loop average for the segment.

Figure 6B:
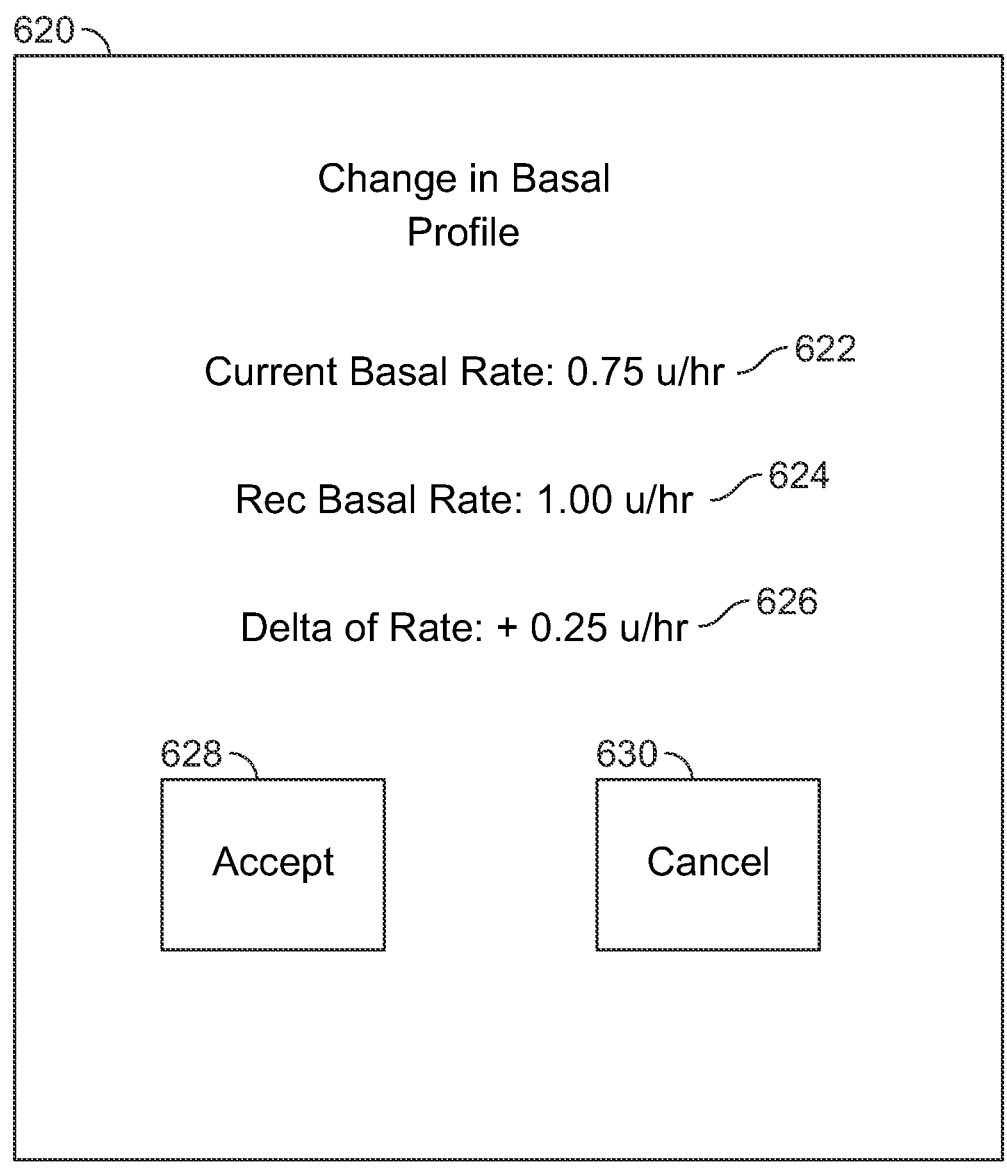
FIG. 6B depicts an illustrative user interface for displaying a suggested adjustment in an open loop basal delivery rate.

At 610, a suggestion of the determined change amount in the basal medicament that is programmed to be delivered during the segment of time in open loop mode may be generated and displayed on a display such as display 109 or display 127. FIG. 6B shows an example of an illustrative display screen 620. The display screen 620 lists the current basal medicament delivery rate 622. In this illustrative case, the current basal medicament delivery hourly rate is 0.75 units/hour. The display screen 620 also shows the recommended basal medicament hourly delivery rate 624. In this illustrative case, the recommended basal medicament delivery rate is derived from the average amount of basal medicament deliveries during the segment and is expressed as an hourly rate of 1.0 units per hour. The difference or a delta between the current basal medicament delivery rate in the recommended basal medicament delivery hourly rate 626 may also be displayed on the display screen 620. The user 108 is thus informed of the proposed change in delivery amounts and can select the accept button 628 to accept the change or the cancel button 630 to reject the change.

At 612, the change in the amount of basal medicament programmed to be delivered during the segment of time in open loop mode is programmatically made. The change may be made in response to the user selecting the accept button 628 or may be automatically made in some embodiments. It should be appreciated that in some exemplary embodiments no suggestion is displayed; rather the change is performed automatically without the user having to approve the change.

Figure 7:
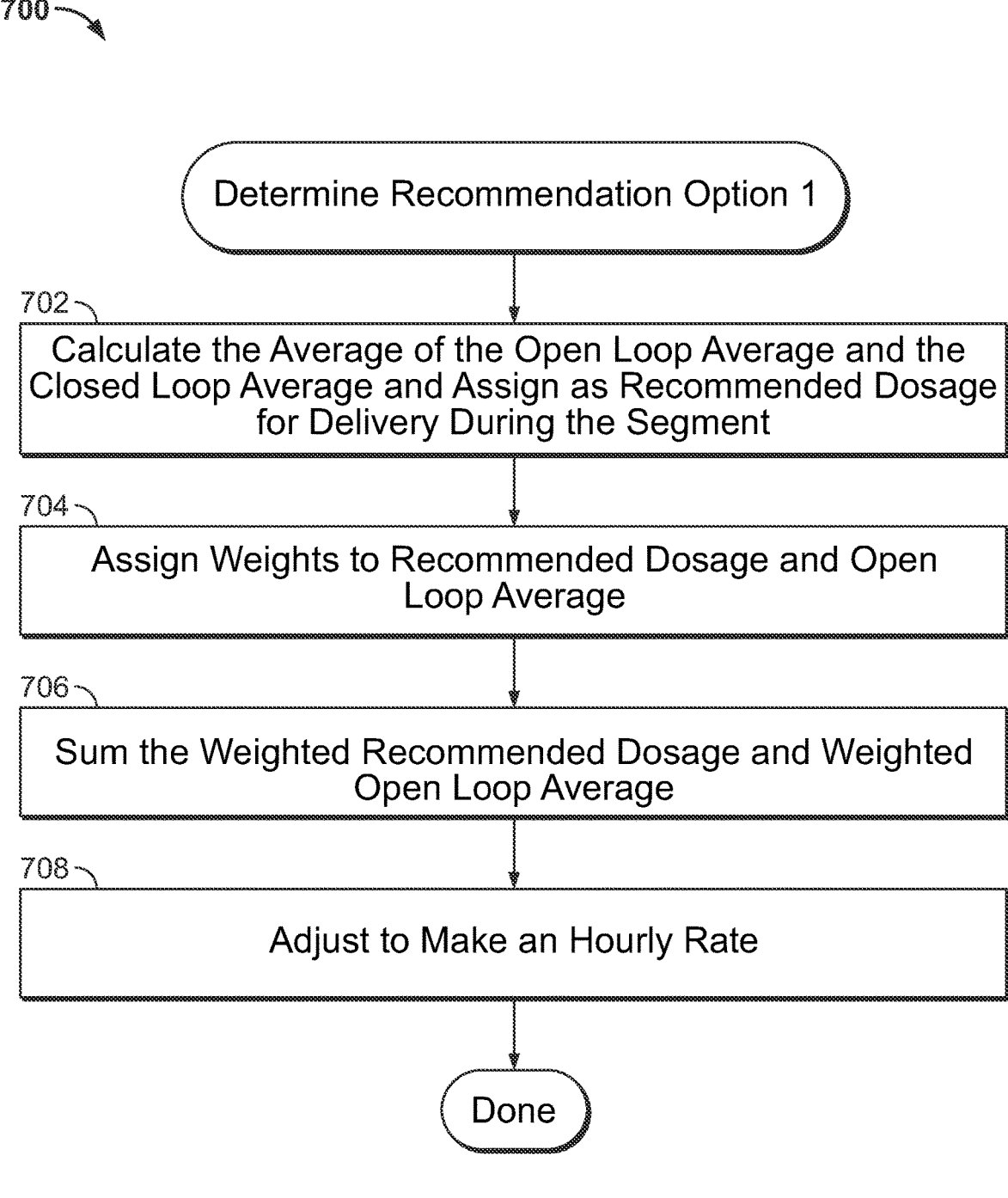
FIG. 7 depicts a flowchart of illustrative steps that may be performed in exemplary embodiments to determine a recommended adjustment to a basal delivery rate in accordance with a first option.

There are different options for determining the magnitude of the change that should be made to the basal medicament delivery amount in the open loop mode. FIG. 7 depicts a flowchart 700 of steps that may be performed in exemplary embodiments in accordance with a first option. At 702, the open loop mode amount currently specified for the current segment and the closed loop mode average are summed and divided by two to produce a recommended medicament delivery amount for the segment. The idea behind this operation is to use the average of the closed loop mode average for the segment and the open loop mode amount for the segment as the recommended amount $TOT_{rec}(j)$. This operation can be expressed as:

$$TOT_{rec}(j) = \frac{TOT_{AID}(j) + TOT_{manual}(j)}{2}$$

In other examples, this recommended amount may completely favor the automated insulin delivery amount $TOT_{AID}$ (j), or an asymmetric weighing of the total manual insulin delivery amount and the automated insulin delivery amount, such as the following equation:

$$TOT_{rec}(j)=A \cdot TOT_{AID}(j)+(1-A) \cdot TOT_{manual}(j)$$

where A is a value between 0 and 1.

At 704, weights are then assigned to the closed loop mode average amount for the segment and to the recommended amount, and at 706 the weighted values are summed. An equation for these operations is:

$$TOT_{manual,new}(j)=B \cdot TOT_{manual}(j)+(1-B)TOT_{rec}(j).$$

where B is the weighing of previous manual basal segment recommendation versus the current recommended amount. A value of 0.8 for B brings about a more gradual movement towards $TOT_{rec}(j)$ so that change is not too rapid and there is not an overshoot. Lastly, at 708, the amount $TOT_{manual,new}(j)$ is divided by the number of hours in the segment to produce an hourly rate. This can be expressed as:

$$b_{rec}(j) = \frac{TOT_{manual,new}(j)}{h_j}.$$

Figure 8:
FIG. 8 depicts a flowchart of illustrative steps that may be performed in exemplary embodiments to determine a recommended adjustment to a basal delivery rate in accordance with a second option.

FIG. 8 depicts a flowchart 800 of illustrative steps that may be performed in exemplary embodiments to determine a changed amount for medicament delivery during a segment j. At 802, the difference between the closed loop average and the open loop amount is determined, and it is determined what range of differences the determined difference falls into. At 804, based on the determined range for the difference, a delta value is assigned. An illustrative formulation for steps 802 and 804, where the medicament is insulin, is:

$$TOT_{delta}(j) = \begin{cases} -0.1 & TOT_{AID}(j) \le 0.8\ TOT_{manual}(j) \\ -0.05 & 0.8\ TOT_{manual}(j) < TOT_{AID}(j) \le 0.95\ TOT_{manual}(j) \\ 0 & 0.95\ TOT_{manual}(j) < TOT_{AID}(j) \le 1.05\ TOT_{manual}(j) \\ 0.05 & 1.05\ TOT_{manual}(j) < I_{AID}(j) \le 1.2\ TOT_{manual}(j) \\ 0.1 & 1.2\ TOT_{manual}(j) < TOT_{AID}(j) \end{cases}$$

In this example, categories for which $TOT_{delta}$ are placed are in increments of 0.1 around 100% of $TOT_{AID}$, but the width of these categories can be varied, such as in increments of 0.75, and can even be made asymmetric to reduce the risk of overcorrection and overdelivery based on higher AID delivery, such as limiting the maximum $TOT_{delta}$ adjustment category to $1.2TOT_{manual}(j) < TOT_{AID}(j)$. Further, in this example, the $TOT_{delta}$ is incremented in units of 0.05 per categorical change—however, these units can vary in quantities, such as 0.1, 0.15, or others.

At 806, the recommended dosage amount is determined from the delta value. One suitable equation is:

$$TOT_{rec}(j)=TOT_{manual}(j)(1+TOT_{delta}(j)).$$

At 808, the recommended dosage is weighted, and the open loop mode amount is weighted. The weighted values are summed, such as:

$$TOT_{manual,new}(j)=B \cdot TOT_{manual}(j)+(1-B)TOT_{rec}(j).$$

At 810, $TOT_{manual,new}(j)$ is converted to an hourly rate by dividing it by the number of hours in the segment j:

$$b_{rec}(j) = \frac{TOT_{manual,new}(j)}{h_j}.$$

Figure 9:
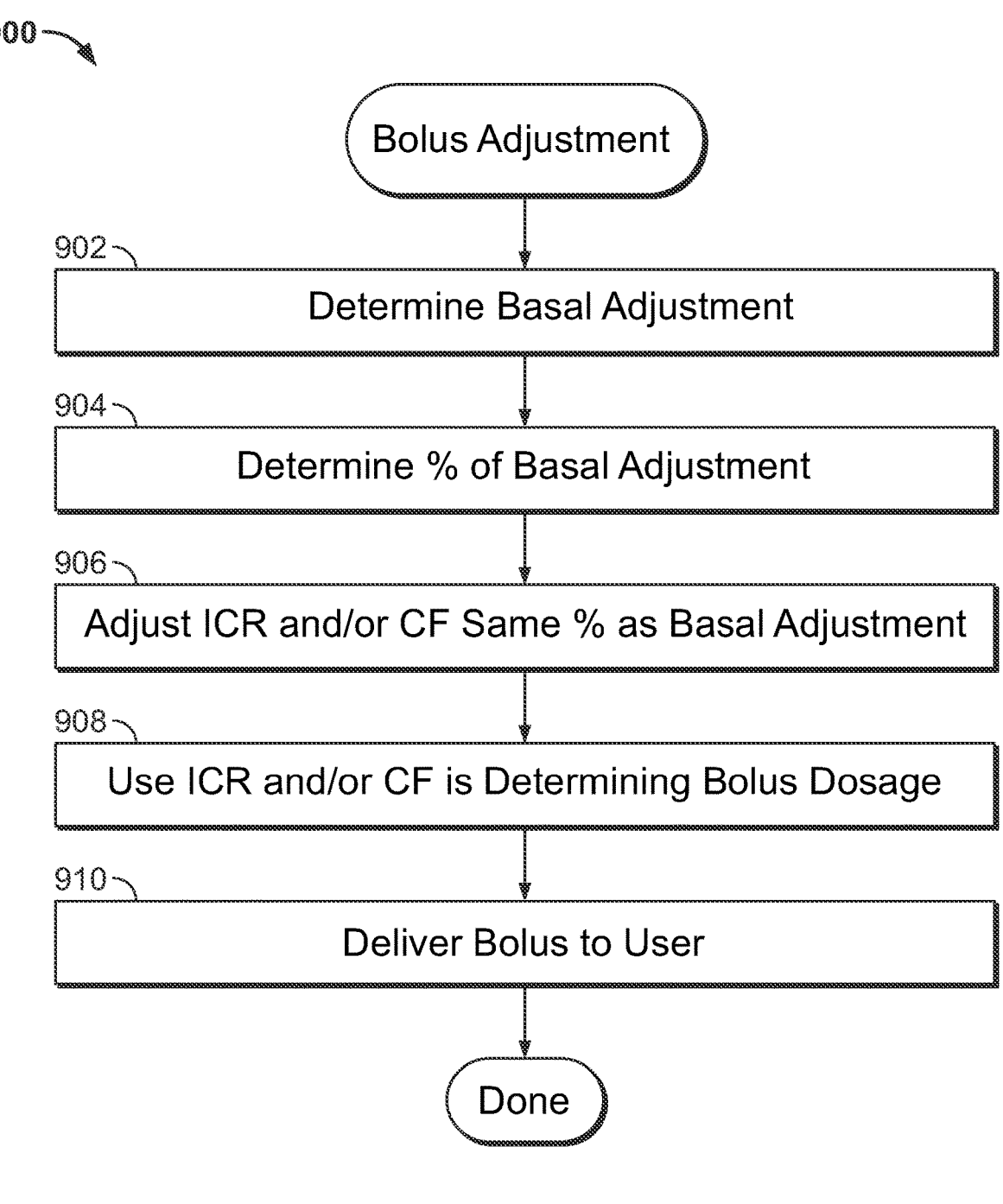
FIG. 9 depicts a flowchart of illustrative steps that may be performed in exemplary embodiments to adjust bolus delivery dosages.

The exemplary embodiments may also change parameters that affect bolus medicament deliveries. FIG. 9 depicts a flowchart 900 of illustrative steps that may be performed to make such adjustments in exemplary embodiments. At 902, the basal medicament delivery rate adjustment for open loop mode is determined as described above relative to FIGS. 6A-8. At 904, the control application 116, 120 determines what percentage of change has occurred in the basal medicament delivery rate for open loop mode as a result of the adjustment. For example, if the basal medicament amount was adjusted from 0.75 units per hour to 1.00 units per hour for a segment, the percentage of change would be +33% (i.e., +0.25/0.75). At 906, the ICR and/or the CF for the user 108 may be adjusted the same percentage as the basal medicament delivery rate (e.g., +33%). The change in the ICR and/or CF for the user 108 will result in a change in bolus amount for the user 108. For example, if the user 108 wishes to compensate for a meal containing 20 grams of carbohydrates and a ICR of 1 unit of insulin to 10 grams of carbohydrates is normally used, a 33% adjustment to the ICR means that 2.66 units of insulin rather than 2.00 units of insulin would be delivered in the bolus after the adjustment. At 908, the adjusted ICR and/or CF are used to determine the medicament bolus dosage, and at 910, the medicament bolus is delivered to the user 108.

In the present application, it should be understood that the term "non-transitory storage medium" may either be a single non-transitory storage medium or multiple non-transitory storage mediums which may be contained in a single device or may be contained (or split up) in different devices, e.g. one non-transitory storage medium in a delivery device and another one in a management device. Similarly, the term "processor" may be a single processor or multiple processors which may be contained in a single device or may be contained (or split up) in different devices, e.g. one processor in a delivery device and another one in a management device.

While exemplary embodiments have been described herein, it should be appreciated that various changes in form and detail may be made without departing from the intended scope as defined in the appended claims.

The invention claimed is:

1. A non-transitory storage medium storing instructions executable by a processor of an electronic device having a display to cause the processor to:

for a medicament delivery device that operates in an open loop mode and a closed loop mode, determine a first average which is an average over a period of a total basal delivery amount of medicament that is delivered to a user by the medicament delivery device in the closed loop mode during a same segment of time in the period;

compare the first average over the period of the total basal delivery amount of the medicament that is delivered to the user by the medicament delivery device in the closed loop mode during the segment of time with an amount of medicament that is to be delivered by the medicament delivery device to the user for the segment of time in the open loop mode to determine a difference; and based on the comparing, perform the following:

display on the display a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference.

2. The non-transitory storage medium of claim 1, wherein the medicament is one of insulin, glucagon like peptide-1 (GLP-1), pramlintide or another agent affecting glucose level.

3. The non-transitory storage medium of claim 1, wherein the programmatically causing the amount of medicament that is programmed to be delivered to the user by the medicament delivery device for the segment of time in the open loop mode to be adjusted comprises:

calculating a second average, which is an average of the first average over the period of the total basal delivery amount of the medicament that is delivered to the user by the medicament delivery device in the closed loop mode during the segment of time and the amount of the medicament that is programmed to be delivered by the medicament delivery device to the user for the segment of time in the open loop mode; and adjusting the amount of the medicament that is programmed to be delivered to the user by the medicament delivery device for the segment of time in the open loop mode based on the second average to produce an adjusted amount of the medicament that is programmed to be delivered to the user by the medicament delivery device for the segment of time in the open loop mode.

4. The non-transitory storage medium of claim 3, wherein the adjusting the amount that is programmed to be delivered to the user by the medicament delivery device for the segment of time in the open loop mode based on the second average to produce an adjusted amount comprises: adding a weighted version of the amount of the medicament that is programmed to be delivered to the user by the medicament delivery device for the segment of time in the open loop mode with a weighted version of the second average to produce a recommended amount of the medicament that is programmed to be delivered to the user by the medicament delivery device for the segment of time in the open loop mode to produce the adjusted amount of the medicament.

5. The non-transitory storage medium of claim 1, wherein a magnitude of the adjusting of the amount of the medicament that is programmed to be delivered to the user by the medicament delivery device for the segment of time in the open loop mode to reduce the difference depends on a magnitude of the difference or a magnitude of a suggested adjusting in a suggestion of the amount of the medicament that is programmed to be delivered to the user by the medicament delivery device for the segment of time in the open loop mode to reduce the difference depends on the magnitude of the difference.

6. The non-transitory storage medium of claim 5, further storing instructions that cause the processor to:

define a plurality of ranges of possible values for the difference;

define a change amount for each range;

determine a selected one of the ranges that the difference falls into; and wherein either the suggestion of the change in the amount of the medicament suggests the change amount of the selected one of the ranges or the programmatically causing the amount of the medicament that is programmed to be delivered to the user by the medicament delivery device for the segment of time in the open loop mode is adjusted by the change amount of the selected one of the ranges.

7. The non-transitory storage medium of claim 1, wherein if the programmatically causing the amount of the medicament that is programmed to be delivered to the user by the medicament delivery device for the segment of time in the open loop mode to be adjusted to reduce the difference is performed, the non-transitory storage medium further stores instructions that cause the processor to display a magnitude of the adjusting of the amount of the medicament that is programmed to be delivered to the user by the medicament delivery device for the segment of time in the open loop mode on the display.

8. An electronic device, comprising:

a non-transitory storage media for storing computer programming instructions;

a processor configured to execute the computer programming instructions to cause the processor to:

for a medicament delivery device that operates in an open loop mode and a closed loop mode, determine a first average which is an average over a period of a total basal delivery amount of medicament that is delivered to a user by the medicament delivery device in the closed loop mode during a same segment of time for intervals in the period;

compare the first average with an amount of medicament that is programmed to be delivered by the medicament delivery device to the user for the segment of time in the open loop mode to determine a difference; and based on the comparing, perform the following:

display on the display a suggestion of a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference.

9. The electronic device of claim 8, wherein the electronic device is one of the medicament delivery device or a management device for the medicament delivery device.

10. The electronic device of claim 8, wherein the medicament is one of insulin, glucagon like peptide-1 (GLP-1), pramlintide or another agent affecting glucose level.

11. The electronic device of claim 8, wherein the processor configured to programmatically causing the amount of medicament that is programmed to be delivered to the user by the medicament delivery device for the segment of time in the open loop mode to be adjusted comprises the processor being configured to:

calculating a second average which is the average of the first average and the amount of the medicament that is programmed to be delivered by the medicament delivery device to the user for the segment of time in the open loop mode; and adjusting the amount of the medicament that is programmed to be delivered to the user by the medicament delivery device for the segment of time in the open loop mode based on the second average to produce an adjusted amount of the medicament that is programmed to be delivered to the user by the medicament delivery device for the segment of time in the open loop mode.

12. The electronic device of claim 8, wherein a magnitude of the adjusting of the amount of the medicament that is programmed to be delivered to the user by the medicament delivery device for the segment of time in the open loop mode to reduce the difference depends on a magnitude of the difference or a magnitude of the suggested adjusting in the suggestion of the amount of the medicament that is programmed to be delivered to the user by the medicament delivery device for the segment of time in the open loop mode to reduce the difference depends on the magnitude of the difference.

13. The electronic device of claim 12, wherein the processor is further configured to execute additional programming instructions to:

define a plurality of ranges of possible values for the difference;

define a change amount for each range;

determine a selected one of the ranges that the difference falls into; and wherein either the suggestion of the change in the amount of the medicament suggests the change amount of the selected one of the ranges or the programmatically causing the amount of the medicament that is programmed to be delivered to the user by the medicament delivery device for the segment of time in the open loop mode is adjusted by the change amount of the selected one of the ranges.

14. The electronic device of claim 8, wherein if the programmatically causing the amount of the medicament that is programmed to be delivered to the user by the medicament delivery device for the segment of time in the open loop mode to be adjusted to reduce the difference is performed, the processor is further configured to execute programming instructions to display a magnitude of the adjusting of the amount of the medicament that is programmed to be delivered to the user by the medicament delivery device for the segment of time in the open loop mode on the display.

15. A non-transitory storage medium storing instructions executable by a processor of an electronic device having a display to cause the processor to:

for a medicament delivery device that operates in an open loop mode and a closed loop mode, determine an average over a period containing intervals of a total basal delivery amount of medicament that is delivered to a user by the medicament delivery device in the closed loop mode during a same segment of time in each of the intervals in the period;

compare the average over the period of intervals (e.g., days) of the total basal delivery amount of the medicament that is delivered to the user by the medicament delivery device in the closed loop mode during the segment of time with an amount of medicament that is programmed to be delivered by the medicament delivery device to the user for the segment of time in the open loop mode to determine a difference;

based on the determined difference, adjust at least one of an insulin to carbohydrate ratio (ICR) of the user or a correction factor of the user; and using the adjusted ICR of the user or the adjusted correction factor of the user in determining a recommended bolus dosage of medicament for the user.

16. The non-transitory storage medium of claim 15, wherein both the ICR of the user and the correction factor of the user are adjusted in the adjusting.

17. The non-transitory storage medium of claim 15, wherein the non-transitory storage medium stores programming instructions to cause the processor to:

based on the comparing, perform the following:

display on the display a suggestion of a change in the amount of medicament that is programmed to be delivered to the user by the medicament delivery device for the segment of time in the open loop mode to reduce the difference, and/or programmatically cause the amount of medicament that is programmed to be delivered to the user by the medicament delivery device for the segment of time in the open loop mode to be adjusted to reduce the difference.

18. The non-transitory storage medium of claim 17, wherein the programming instructions cause the processor to perform both the displaying on the display of the suggestion and the programmatically causing the amount of medicament that is programmed to be delivered to the user by the medicament delivery device for the segment of time in the open loop mode to be adjusted to reduce the difference.

19. The non-transitory storage medium of claim 17, wherein the medicament is one of insulin, glucagon like peptide-1 (GLP-1), pramlintide or another agent affecting glucose level.

20. The non-transitory storage medium of claim 17, wherein the processor is part of a management device for the medicament delivery device.

* * * * *